US00PP23692P3

(12) United States Plant Patent
Bédard

(10) Patent No.: US PP23,692 P3
(45) Date of Patent: Jul. 2, 2013

(54) MINIATURE ROSE PLANT NAMED 'WEKWISOGOMA'

(50) Latin Name: *Rosa hybrida*
Varietal Denomination: WEKwisogoma

(75) Inventor: Christian Bédard, Brea, CA (US)

(73) Assignee: Weeks Roses, Pomona, CA (US)

( * ) Notice: Subject to any disclaimer, the term of this patent is extended or adjusted under 35 U.S.C. 154(b) by 73 days.

(21) Appl. No.: 13/373,853

(22) Filed: Dec. 2, 2011

(65) Prior Publication Data

US 2013/0145508 P1 Jun. 6, 2013

(51) Int. Cl.
*A01H 5/00* (2006.01)

(52) U.S. Cl.
USPC ..... Plt./121; Plt./101; Plt./116

(58) Field of Classification Search
USPC ..... Plt./101, 116, 121
See application file for complete search history.

*Primary Examiner* — Susan McCormick Ewoldt
(74) *Attorney, Agent, or Firm* — McKee, Voorhees & Sease, P.L.C.

(57) ABSTRACT

A new variety of Miniature rose suitable for garden decoration, having flowers of incandescent pink coloration.

1 Drawing Sheet

Classification: The present invention relates to a new *Rosa hybrida* plant.

Variety denomination: The new plant has the varietal denomination 'WEKwisogoma'.

BACKGROUND OF THE INVENTION

This invention relates to a new and distinct variety of Miniature Rose. It has as its seed parent the variety known as 'SAVawin' (U.S. Plant Pat. No. 5,691) and as its pollen parent the variety known as 'KORfalt' (not patented).

SUMMARY OF THE INVENTION

Among the features which distinguish the new variety from other presently available and commercial rose cultivars known to the inventor are the following combinations of characteristics: its hairy receptacle, its very abundant bloom, its excellent color stability throughout the life of the flower and its moderately large flower size for the class. The plant has a rounded bushy growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKwisogoma' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'SAVawin' by the following combination of characteristics: whereas 'WEKwisogoma' bears double flowers (about 15 to 24 petals) of incandescent pink coloration, 'SAVawin' bears double flowers of unusual spinel red coloration with significantly heavier petalage (about 30 to 36 petals). The new variety bears moderately large flowers for its class (about 5.1 to about 6.8 cm. in diameter), whereas the seed parent bears significantly smaller flowers (about 4.5 to about 5.1 cm. in diameter).

The new variety may be distinguished from its pollen parent, 'KORfalt' by the following combination of characteristics: whereas 'WEKwisogoma' bears double flowers (about 15 to 24 petals) of incandescent pink coloration, 'KORfalt' bears double flowers of deep gold yellow coloration with significantly heavier petalage (about 25 to 30 petals).

COMPARISON WITH THE CLOSEST COMMERCIALLY AVAILABLE CULTIVAR

The new variety may be distinguished from its closest commercially available cultivar, 'MORyou' (U.S. Plant Pat. No. 8,200) by the following combination of characteristics: whereas 'WEKwisogoma' bears moderately large flowers for its class (about 5.1 to about 6.8 cm. in diameter) of incandescent pink coloration, 'MORyou' bears significantly smaller flowers (about 4.0 to about 4.5 cm. in diameter) of deep pink to medium red coloration. The new variety has a rounded bushy medium height to somewhat tall growing habit (about 72 to about 82 cm. in height), whereas the closest commercially available cultivar has a dwarf, bushy and upright significantly shorter growing habit (about 31 to about 36 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong short to medium length stems (about 9.0 to about 31.0 cm.). Outdoors, the plant blooms very abundantly and nearly continuously during the growing season. The flowers have a slight fruity to apple-like fragrance.

BUD

The peduncle is about 2.0 to about 5.1 cm. in length, of slender to average caliper (about 0.15 to about 0.2 cm. in diameter), and usually erect. It is somewhat rough, with many stipitate glands and few hairs. Peduncle color is between 146C and 146B often lightly suffused, especially on the side exposed to the sun, with between 187B and 183B.

Before the calyx breaks, the bud is about 0.8 to about 1.4 cm. in diameter at the widest point, about 1.3 to about 1.7 cm. in length, and pointed to somewhat ovoid in shape. The surface of the bud bears between 4 to 7 foliaceous appendages with some stipitate glands and few hairs, usually with slender entire foliaceous parts extending beyond the tip of the bud about ½ or more of its length. Bud color is between 146A and 146B often moderately suffused, especially on the side exposed to the sun, with between 187B and 187A.

The sepals are about 2.1 to about 3.1 cm. in length and about 0.6 to about 0.9 cm. in width at the widest point. The outer surface color of the sepal is between 146A and 146B often moderately suffused, especially on the side exposed to the sun, with between 187B and 187A. The inner surface color of the sepal is near 146C broadly bordered by near 139A. After the sepals open, the inner surface color is often heavily suffused, especially on the area exposed to the sun, with between 187A and 187B. The inner surface of the sepal is covered with fine wooly tomentum; sepal margins are lined with some stipitate glands and many hairs.

The receptacle of the flower is of medium length (about 0.3 to about 0.5 cm.) and somewhat heavy in caliper (about 0.4 to about 0.7 cm. in diameter). The receptacle is urn-shaped in form. Its surface is smooth with some hairs and with moderately thin fleshy walls. The receptacle color is between 144A and 146B sometimes lightly suffused, especially on the side exposed to the sun, with between 187B and 183B.

As the petals open (after the calyx breaks), the bud is about 1.3 to about 1.7 cm. in diameter at the widest point, about 1.8 to about 2.6 cm. in length, and pointed to moderately ovoid in form. The color of the under surfaces of the newly opened petals is between 60A and 53A sometimes moderately suffused with between 187A and 187B. At the point where the petal attaches, there is a small zone of between 1D and 154D. The color at the base of the upper surface of the newly opened petals is between 24C and 28D gradually suffusing toward the middle of the petal with between 53C and 53D often moderately suffused with between 187B and 187A. At the point where the petal attaches, there is a moderately small zone of between 3C and 4B.

BLOOM

When fully open, the bloom ranges from about 5.1 to about 6.8 cm. in diameter. Petalage is double with about 15 to 24 petals and about 2 to 9 petaloids irregularly arranged. When partially open, the bloom form is ovoid to somewhat high centered, and the petals are loosely spiraled to somewhat cupped with petal edges moderately reflexed outward. When fully open, the bloom form is cupped, and the petals are loosely cupped with petal edges moderately reflexed outward.

PETALS

The substance of the petals is moderately heavy and of medium thickness, with upper surfaces moderately satiny to somewhat velvety and under surfaces slightly shiny to almost matte. The petals are about 2.1 to about 2.9 cm. in length and about 1.3 to about 3.1 cm. in width at the widest point. Petal margins are entire.

The outer petals are nearly rounded to somewhat obovate in shape with rounded apices.

The inner petals are obovate to moderately oblanceolate in shape with rounded apices.

Petaloids are about 0.8 to about 2.4 cm. in length and about 0.5 to about 1.4 cm. in width at the widest point. Petaloids are irregularly shaped moderately oblanceolate to somewhat subulate with rounded apices.

NEWLY OPENED FLOWER

The under surface color of the outer petals is between 53B and 57A sometimes moderately suffused on the outermost petals with between 187B and 53A. At the point where the petal attaches, there is a small zone of between 3D and 4C. The color at the base of the upper surface of the outer petals is between 18A and 18B gradually suffusing toward the middle of the petal with between 53C and 62A often moderately suffused with between 187B and 57A. At the point where the petal attaches, there is a moderately small zone of between 3C and 4B.

The under surface color of the intermediate and inner petals is between 53C and 57A. The color at the base of the upper surface of the intermediate and inner petals is between 18A and 18B gradually suffusing toward the middle of the petal with between 53C and 62A often lightly suffused with between 187B and 57A.

The under and upper surface colors of the petaloids are similar in coloration to the upper and under surfaces of the intermediate and inner petals.

The general tonality of the newly opened flower is between 18A and 18B at the base gradually suffusing toward the middle of the petal with between 53C and 62A often lightly suffused with between 187B and 57A.

THREE-DAY-OLD FLOWER

The under surface color of the outer petals is between 60B and 61C sometimes moderately suffused on the outermost petals with between 187B and 60A. At the point where the petal attaches, there is a small zone of between 4D and 155A. The color at the base of the upper surface of the outer petals is between 155B and 155A gradually suffusing toward the middle of the petal with between 57B and 67C often moderately suffused with between 60A and 61B. At the point where the petal attaches, there is a moderately small zone of near 2D.

The under surface color of the intermediate and inner petals is between 60D and 61C. The color at the base of the upper surface of the intermediate and inner petals is between 11D and 19D gradually suffusing toward the middle of the petal with between 57B and 67C often lightly suffused with between 60A and 61B.

The under and upper surface colors of the petaloids are similar in coloration to the upper and under surfaces of the intermediate and inner petals.

The general tonality of the three-day-old flower is between 11D and 19D at the base gradually suffusing toward the middle of the petal with between 57B and 67C often lightly suffused with between 60A and 61B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 108) and are arranged regularly about the pistils; a few are mixed with petaloids. The filaments are of medium to long length (about 0.4 to about 1.1 cm.) most with anthers. Filaments are near 15C in color sometimes lightly suffused with near 44C. The anthers are moderately small for the class and all open approximately at the same time. Anther color when immature is near 23B on the external part and near 12D on the internal part. Anther color at maturity is near 165B on the external part and near 200A on the internal part. Pollen is moderate and between 16B and 20B in color.

FEMALE REPRODUCTIVE ORGANS

Pistils vary in number (average about 110). The styles are moderately even, average in length (about 0.4 to about 0.6 cm.), thin in caliper, and moderately columnar to loosely separated. Stigma color is between 2C and 1 C. Style color is between 150C and 154C sometimes lightly suffused with near 53C. Ovaries are usually all enclosed in the calyx.

Hips have not been observed on this variety when grown in Pomona, Calif.

FOLIAGE

The compound leaves are usually comprised of three to seven leaflets and are borne abundantly. The seven-leaflet leaves are about 5.3 to about 11.9 cm. in length and about 3.1 to about 6.7 cm. in width at the widest point, moderately leathery to somewhat crisp in texture, and very glossy in finish on the upper side and matte in finish on the under side. The terminal leaflets are about 1.6 to about 4.2 cm. in length and about 1.4 to about 2.4 cm. in width at the widest point, shaped ovate with acute apices and rounded bases. Their margins are usually simply serrate.

The upper surface color of the mature leaf is between 139A and 147A. The under surface color of the mature leaf is between 147B and 137C. The upper surface color of the young leaf is between 137A and 144A, sometimes moderately suffused, usually on the edge of the leaflets, with between 187B and 183A. The under surface color of the young leaf is between 147B and 146B, sometimes lightly suffused with between 187B and 183A.

The rachis is somewhat light in caliper and moderately rough. The upper side is deeply grooved with few hairs and stipitate glands on the edges of the grooves. The under side of the rachis is moderately rough with very few stipitate glands and few small prickles. The rachis color is near 146C on the under side and near 137A on the upper side often moderately suffused on the young leaf with between 187B and 183A.

The stipules are about 0.8 to about 1.3 cm. in length and of medium width (about 0.3 to about 0.4 cm.) with somewhat short straight points that usually turn out at an angle of more than 45 degrees. The under and upper surface color of the stipule is between 137A and 137B.

The petiole is somewhat light in caliper and smooth. The upper side is deeply grooved with few hairs and stipitate glands on the edges of the grooves. The under side of the petiole is smooth with very few stipitate glands. The petiole is about 0.4 to about 0.8 cm. in length and about 0.1 to about 0.15 cm in width at the widest point. The petiole color is near 146C on the under side and near 137A on the upper side often moderately suffused on the young leaf with between 187B and 183A.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a rounded bushy medium height to somewhat tall growing habit (about 72 to about 82 cm. in height and about 52 to about 62 cm. spread at the widest point), with very full branching. It displays vigorous growth and the canes are of moderately heavy caliper for the class (about 1.0 to about 2.0 cm. in diameter at the widest point).

The color of the major stems is between 146B and 146C. They bear few large prickles that are about 0.6 to about 0.9 cm. in length. The large prickles are angled moderately to somewhat hooked downward with a somewhat short moderately broad oval base; prickle color is between 164A and 166C. The major stem bears few small prickles of similar shape and coloration.

The color of the branches is between 146B and 147A. They bear few large prickles which are of similar shape to the large prickles on the major stems. The large prickles are about 0.4 to about 0.6 cm. in length. Prickle color is between 161B and 162B sometimes lightly suffused with near 187D. The branches bear no small prickles.

The color of the new shoots is between 146B and 147A sometimes moderately suffused with between 187B and 187A. They bear few large prickles which are of similar size and shape to the large prickles on the major stems; prickle color is between 153A and 151 A usually heavily suffused with between 187B and 187C. The shoots bear no small prickles.

I claim:

1. A new and distinct Miniature rose plant of the variety substantially as described and illustrated herein.

* * * * *

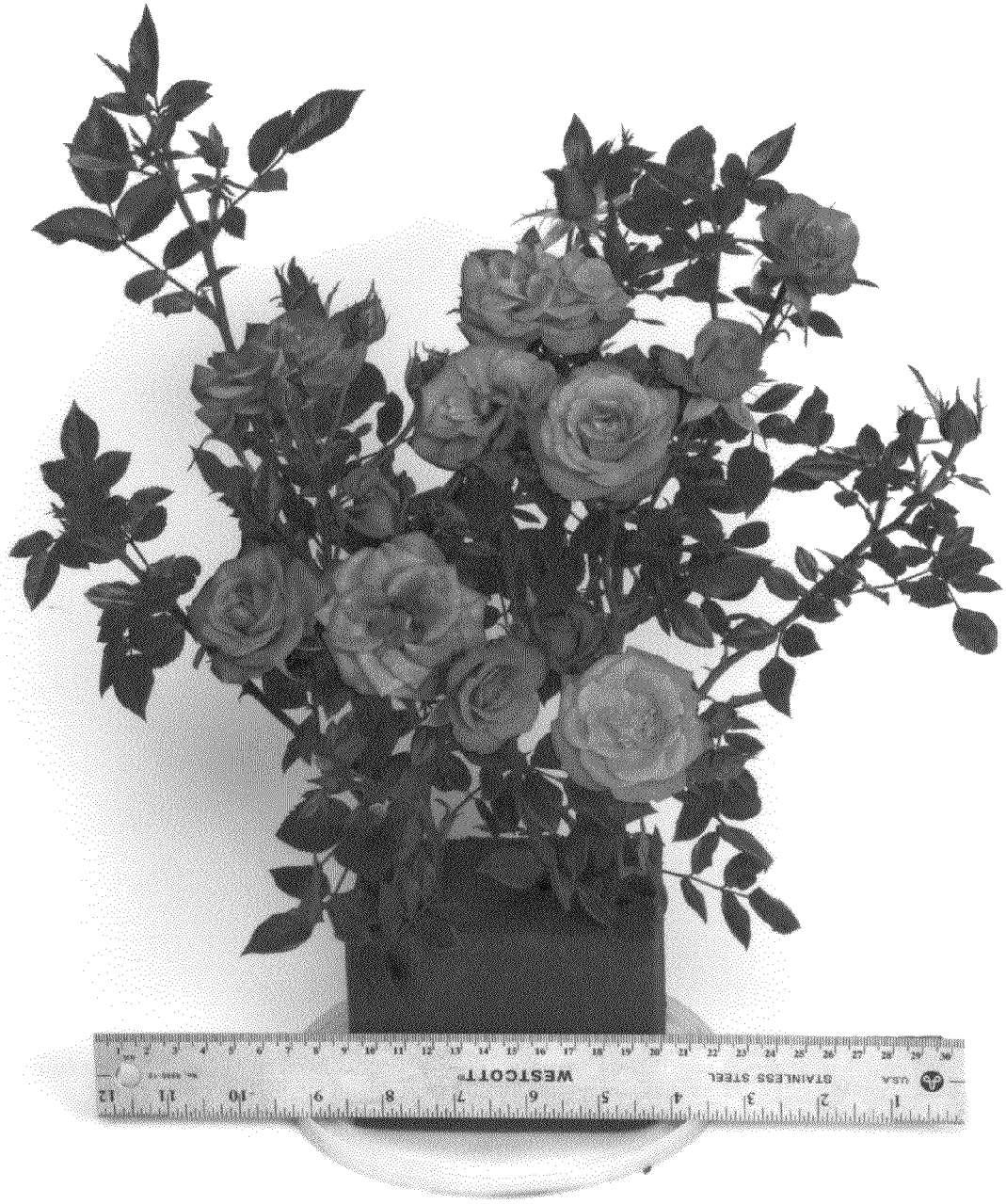
USA
STAINLESS STEEL
WESTCOTT